United States Patent [19]

Puglia et al.

[11] 4,327,077

[45] Apr. 27, 1982

[54] COMPRESSED CHEWABLE ANTACID TABLET AND METHOD FOR FORMING SAME

[75] Inventors: Wayne J. Puglia, Bellerose Village; Kanit J. Patanasinth, Tarrytown; Andrew T. Lombardo, Bronx; Walter Vink, Purdys Station, all of N.Y.

[73] Assignee: Life Savers, Inc., New York, N.Y.

[21] Appl. No.: 268,314

[22] Filed: May 29, 1981

[51] Int. Cl.³ .................. A61K 9/20; A61K 9/42; A61K 33/08; A61K 33/10

[52] U.S. Cl. .................. 424/38; 424/154; 424/156; 424/157; 424/158; 424/155; 424/361; 424/365; 424/280; 424/266; 424/263; 424/252; 424/255; 424/344; 424/147; 424/230; 424/330; 426/660

[58] Field of Search .............. 424/38, 154–158, 424/361, 365

[56] References Cited

U.S. PATENT DOCUMENTS

| | | | |
|---|---|---|---|
| 780,226 | 1/1905 | Pink | 424/38 |
| 3,253,988 | 5/1966 | Scott | 424/154 |
| 3,384,546 | 5/1968 | Palermo | 424/156 |
| 3,452,138 | 6/1969 | Granatek et al. | 424/156 |
| 3,536,074 | 10/1970 | Auf Hauser | 424/38 |
| 3,843,778 | 10/1974 | Diamond et al. | 424/38 |
| 4,112,066 | 9/1978 | Hussein | 424/48 |
| 4,115,553 | 9/1978 | Rubino et al. | 424/156 |
| 4,163,777 | 8/1979 | Mitra | 424/21 |
| 4,199,560 | 4/1980 | Gyarmati et al. | 424/19 |
| 4,230,693 | 10/1980 | Izzo et al. | 424/156 |
| 4,271,142 | 6/1981 | Puglia et al. | 424/14 |

FOREIGN PATENT DOCUMENTS

| | | | |
|---|---|---|---|
| 8869 | of 1888 | United Kingdom | 424/15 |
| 26894 | of 1908 | United Kingdom | 424/156 |
| 392 | of 1913 | United Kingdom | 424/156 |
| 543309 | 2/1942 | United Kingdom | 424/38 |
| 1414121 | 11/1975 | United Kingdom | 424/157 |
| 1538280 | 1/1979 | United Kingdom | . |

*Primary Examiner*—Shep K. Rose
*Attorney, Agent, or Firm*—Richard Kornutik

[57] ABSTRACT

An improved compressed soft chewable tablet is provided, which may contain an antacid or other active ingredient, has good flexibility, is breakage resistant and disintegrates immediately upon chewing. The tablet of the invention is formed of particles of a recrystallized fatty material, such as chocolate, a bulking material such as sugar or an active ingredient, such as an antacid, bound up in the particles of recrystallized fatty material, and a direct compaction vehicle which binds the particles of recrystallized fatty material and bulking material, under compression, into a chewable tablet.

12 Claims, No Drawings

COMPRESSED CHEWABLE ANTACID TABLET AND METHOD FOR FORMING SAME

CROSS REFERENCE TO RELATED APPLICATIONS

This application contains subject matter related to, but distinctly different from, the subject matter of U.S. Pat. No. 4,271,142 granted on U.S. application Ser. No. 170,469 filed July 21, 1980, to Puglia et al., U.S. application Ser. No. 137,944 to Witzel et al., filed Apr. 7, 1980 and U.S. application Ser. No. 175,179 to Morris et al., filed Aug. 4, 1980.

The present invention relates to a compressed chewable tablet, such as an antacid tablet, which is breakage resistant, yet quickly disintegrates in the mouth to a smooth creamy pleasant-tasting emulsion, devoid of the grittiness normally associated with antacids and other chewable tablets.

BACKGROUND OF THE INVENTION

Palatability and "mouth feel" are extremely important factors in formulating chewable tablets, especially pharmaceutical dosage forms. Many pharmaceutical and confectionery tablets are designed to be chewed either to provide proper flavorants or to increase the surface area of a particular drug to permit rapid activity in the digestive or circulatory system. Consequently, tablet formulations must be developed which will satisfy certain basic requirements:

sufficient cohesive properties to form a firm tablet under compression
sufficient lubrication to prevent binding in the die cavities
adequate flow to provide uniform weight
absence of sticking under compression
uniform drug dose and release after ingestion
  production capability on high speed equipment Furthermore, many pharmaceutical ingredients usually have both an unpleasant mouth feel and unpalatable taste due to chalkiness, grittiness, dryness and astringent properties of these materials. Accordingly, the practical value of these materials is substantially diminished since patients finding them objectionable may fail to take them as prescribed.

In an effort to overcome the above problems, flavorings have been employed with pharmaceuticals and especially antacids and vitamins to either mask or override the unpleasant dryness and astringent properties and chalkiness associated therewith. Unfortunately, it has been found that the flavoring merely masks the unpleasant taste, but the chalkiness, grittiness, dryness and astringent properties still remain.

U.S. Pat. No. 3,843,778 to Diamond et al. discloses a technique for coating antacid particles with a water insoluble, inert, non-toxic hydrocarbon oil which is formulated into suspensions or tablets which are said to be substantially free of the impalatable "mouth feel" properties associated with antacids. An electronegative agent, such as a surfactant selected from an alkyl aryl sulfonate, or an alkyl sulfate or sulfonate, or sulfonated amides or amines, or sulfated or sulfonated esters or ethers, or a dioctyl sulfosuccinate, or a hydrated aluminum silicate, such as bentonite or kaolin, is employed to aid in adhering the oil to the electropositively charged antacid particles.

U.S. Pat. No. 3,253,988 to Scott discloses an orally administrable antacid formed of oils or fats, that is, esters of higher fat acids and a trihydric alcohol, in combination with antacids. The Scott antacid may be in the form of a waxy solid, an emulsion or suspension.

U.S. Pat. No. 4,230,693 assigned to Armour-Dial, Inc. describes an antacid tablet containing fat, antacid, sugar, starch and water. It is prepared through a wet granulation technique and utilizes fats with melting points above body temperature. Also, the tablet press employed must be heated to 105°-120° F. to avoid sticking and adherence to punch faces. The antacid tablet is said to be prepared by mixing the antacid ingredient, water, sugar and fat to provide a powdered mixture, forming the mixture into a tablet shape and applying a pressure of from 50 to 600 psi to the mixture, the tabletting machine, including the punch elements of the presses, preferably being maintained at an elevated temperature.

The tablet may also be prepared by mixing the fat in liquid form and the antacid with the sugar and water, cooling the resultant mixture to a temperature of below 40° F. and then passing the mixture through a mill to obtain a powdered mixture which is then formed into tablets.

Generally, tablets are normally made by direct compression wherein a mixture of tabletting compounds including active ingredient, flavor, bonders, etc., are fed to a die chamber of a tablet press and a tablet is formed by direct compaction. Hardness of the resulting tablet is a direct function of the compression pressure employed. Where it has been desired to produce a so-called "soft" tablet, that is, one which has easy bite-through, a disintegrator, such as alginic acid, is added to the pre-tablet mix. Alternatively, a soft tablet has been formed by employing reduced compression temperatures. The result in each instance has been essentially the same, namely, production of a softer tablet which is very fragile and brittle and is easily chipped.

It has also been suggested to employ a fatty material in the pre-tablet mix to attain tablet softness. However, it has been found that the addition of fats or oils to the pre-tablet mix causes tabletting ingredients to adhere to the die chamber and significant reduction in the bonding action of the bonders present in the mix.

DESCRIPTION OF THE INVENTION

In accordance with the present invention, a unique compressed chewable tablet is provided which has excellent hardness and flexibility, is breakage and chip resistant and yet may be easily chewed and quickly disintegrated and dissolved in the mouth. The compressed chewable tablet of the invention includes a particulate recrystallized fatty material having a bulking material or agent bound up therein and a direct composition vehicle which binds the combined particles of recrystallized fatty material and bulking material, under compression, into a chewable tablet.

In addition, in accordance with the present invention, a method is provided for making the above compressed chewable tablet which method includes the steps of melting the fatty material, adding the bulking material to the melt, allowing the melted fatty material mixed with the bulking material to recrystallize and form particles of such mixture, and mixing the particles of recrystallized fatty material with direct compaction vehicle, reducing average particle size of the mixture, if necessary, to within the range of from about 200 to about 1100 microns, and then forming the compressed chewable tablet from such mixture.

It has been found that the difference in density and temperature of the bulking material added to the melted fatty material causes the melted material to recrystallize back to a soft powder.

The fatty material employed herein will preferably be in the form of chocolate or a synthetic chocolate, such as compound coating or "Ice-Cap coating" (Nestle's synthetic chocolate formed of hydrogenated fat, emulsifier, flavor, sugar and milk solids). These fatty materials are preferred because they provide excellent flavor and sweetness with the requisite amounts of fats, (in the form of hydrogenated fats), that is, fats in an amount of from about 5 to about 20% and preferably from about 10 to about 14% by weight of the finished chewable tablet. Since the hydrogenated fats account for about 30 to about 40% of the chocolate or synthetic chocolate, the chocolate materials may be present in an amount of from about 20 to about 55% and preferably from about 35 to about 45% by weight of the finished compressed tablet. It has been found that where larger amounts of fats are employed, the fats must be pretreated and absorbed on a carrier, such as cornstarch, to facilitate compaction. In the present invention, no such pretreatment is required.

Other fatty materials which may be employed herein in the amounts set out above are those which may be melted, mixed with bulking agent and thereafter recrystallized and comminuted into a fine powder. These other fatty materials include fats or oils of animal, vegetable or mineral origin which are substantially water-insoluble, inert, non-toxic hydrocarbon fats and oils and derivatives thereof and may comprise any of the commonly commercially available fats or oils approved by the Food & Drug Administration and having melting points constant with desired mouth feeling factors, such as melting points ranging from 80° to 110° F. and need not be limited to melting points above body temperature. Examples of these additional fats and/or oils suitable for use herein include hydrogenated tallow.

The direct compaction vehicle (which must be dry blended into the granulation subsequent to recrystallizing the fatty material admixed with the bulking material) may include tablet excipients resulting from pretreatment via a wet granulation technique, tabletting grade sorbitol and mannitol, mixtures thereof, dextrose monohydrate, such as Cantab ® or Cerelose ® 2001 (registered trademarks of UNIVAR and Corn Products Corp., respectively), corn syurp solids having a DE of from 38 to 45, anhydrous lactose, Encompress (blends of dicalcium phosphate dihydrate), diPac (co-crystallized sucrose with modified dextrins), sucrose, invert sugar and mixtures thereof, with tabletting sugar and dextrose monohydrate being preferred.

The direct compaction vehicle will be present in an amount of within the range of from at least about 25 to about 60%, and preferably from about 30 to about 40% by weight of the final compressed tablet.

As indicated, it is essential in forming the compressed chewable tablet of the invention that the direct compaction vehicle be added after the fatty material has recrystallized. Should the fatty material be in liquid form when the direct compaction vehicle is added, the fatty material would coat the direct compaction vehicle and render it useless as a binder and compaction vehicle.

The nature and amount of bulking material employed will depend upon the nature of the final product. Generally, the bulking material will be in powdered form (average particle size of from about 25 to about 250 microns) and will be present in an amount within the range of from about 15 to about 45% and preferably from about 25 to about 35% by weight of the finished compressed tablet.

Where the compressed chewable tablet of the invention is to be in the form of a confection, the bulking material may comprise confectioner's sugar, sorbitol, mannitol, hydrogenated starch hydrolysate (Lycasin), isomaltitol (Palatinit), polydextrose, mixtures of any of the above, or other known sweet materials. In the case of a confection, the bulking material will be present in an amount within the range of from about 15 to about 45% and preferably from about 25 to about 35% by weight of the finished compressed tablet.

In another embodiment of the present invention, the bulking material will comprise an active ingredient, such as antacids, vitamins, laxatives, antiflatulents, aspirin, acetaminophen, appetite depressants and the like. Compressed tablets of the invention containing the above active ingredients will have a non-chalky non-gritty pleasant taste and when exposed to saliva in the mouth will convert to an emulsion or colloidal suspension and thus behaves as would a liquid. Also, since the compressed tablet of the invention will disintegrate rapidly in hot solution, it would be an advantageous portable vehicle for flavoring beverages where the inclusion of a fat or fat based system would improve palatibility. Examples of such vehicles would be tabletted coffee whiteners and flavorants, bouillon type soups, cream type soups, and the like.

The active ingredient, depending upon the specific properties thereof, will generally comprise from about 10 to about 50% and preferably from about 15 to about 30% by weight of the final compressed tablet.

In preferred embodiments, the bulking material will comprise an antacid material as the active ingredient which will be present in an amount within the range of from about 10 to about 50% by weight and preferably from about 15 to about 35% by weight of the final compressed tablet. Examples of antacids suitable for use herein comprise any relatively water-insoluble antacid acceptable to the Food & Drug Administration, such as, aluminum carbonate, aluminum hydroxide (or as aluminum hydroxide-hexitol stabilized polymer, aluminum hydroxide-magnesium hydroxide codried gel, aluminum hydroxide-magnesium trisilicate codried gel, aluminum hydroxide-sucrose powder hydrated), aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

Preferred antacids include aluminum hydroxide, calcium carbonate, magnesium carbonate and mixtures thereof as well as magnesium hydroxide.

Any emulsifier or surfactant approved for use in foods by the Food & Drug Administration and having an HLB value of 8 and above, may optionally be employed in the chewable tablets of the invention in amounts ranging from about 0.05 to about 2.5% by weight and preferably in amounts ranging from about 0.1 to about 1.0% by weight based on the final chewable tablet formulation.

Examples of emulsifiers or surfactants suitable for use herein to aid in release of the antacid ingredient include alkyl aryl sulfonate, or alkyl sulfates, or sulfonated amides or amines, or sulfated or sulfonated esters or ethers, or alkyl sulfonates, or dioctyl sulfosuccinate and the like, or a hydrated aluminum silicate such as micronized bentonite or kaolin, or Cab-O-Sil (which is silica pigment solid under the trademark of Cab-O-Sil by Cabot Corporation of Boston, Mass.), Quso (which is a microfine silica sold under the trademark Quso by Philadelphia Quartz Co. of Philadelphia, Pa.), and the like, triglycerol monostearate, triglycerol monoshortening, octaglycerol monooleate, octaglycerol monostearate, decaglycerol decaoleate, Span 60, and Tween 60 and 80.

Preferred are the polyoxyethylene sorbitan fatty acid esters, such as the stearates, oleates, palmitates and the like, for example Tween 60 and 80, as well as octaglycerol monooleate, triglycerol monostearate and triglycerol monoshortening.

The essential ingredient present for masking chalkiness, grittiness, dryness and astringent properties in the preferred antacid tablet of the invention will be a natural or synthetic fatty type or other flavorant, examples of which include cocoa, chocolate, especially mint chocolate, butter, milk, cream, vanillin butter fat, egg or egg white, as well as peppermint oil, wintergreen oil, spearmint oil and the like, with the chocolate or vanilla being preferred. Where the above flavorant is employed in amounts within the range of from about 0.05 to about 1% and preferably from about 0.2 to about 0.8% by weight of the tablet, the flavorant, together with the fatty material described above provides an enhanced effect in minimizing grittiness and enhancing texture and mouth feel.

The fatty materials comprising the above flavors may be employed as the fatty material in the compressed tablet of the invention.

The antacid tablets as well as the other compressed tablets of the invention may also include one or more other pharmaceutically acceptable agents, as desired, such as sweetening agents, including sugars, sugar alcohols, hydrogenated starch hydrolysates (Lycasin) and synthetic sweeteners, such as sorbitol, xylitol, saccharin salts, free acid form of saccharin, cyclamate salts, free cyclamic acid, dihydrochalcones, L-aspartyl-L-phenylalanine methyl ester, isomaltitol (Palatinit), as well as coloring agents, other flavoring agents, disintegrating agents, such as starch, other binding agents, lubricants, such as calcium stearate, stearic acid, magnesium stearate (0.5 to 3% by weight), antioxidants, such as butylated hydroxy toluene, antiflatulents, such as simethicone, bulking agents such as polydextrose and the like.

The antacid tablet as well as the other types of compressed tablets of the invention may be sealed in a sealant, such as gum arabic or starch to prevent breakage. Furthermore, the tablet may be spray coated or otherwise coated with chocolate or other standard confections coating to prevent breakage during shipment and handling and to further decrease the chalky nature of the tablet. In addition, a confections glaze may be applied over the coating to prevent premature melting during handling.

It is preferred that in formulating the compressed tablet of the invention that the antacid material as well as other active ingredients have a primary particle size of less than 100 millimicrons and more preferably less than 50 millimicrons, and that where mixing is required during the preparation of the tablet that the antacid material or other active ingredient, fatty material, direct compaction vehicle, emulsifier, flavorant, and other ingredients be intensively mixed until complete homogeneity is achieved.

The following are preferred chewable tablet formulations in accordance with the present invention:

| Preferred Compressed Tablet Confection | |
|---|---|
| Ingredient | Parts by Weight of Finished Tablet |
| Fatty material (chocolate or Ice-cap coating (Nestle's)) | 20 to 55 |
| Emulsifier | 0.05 to 2.5 |
| Bulking material (Sugar) | 15 to 45 |
| Flavor (preferably chocolate) | 0.05 to 1 |
| Direct compression vehicle | 25 to 60 |

| Preferred Compressed Tablet Antacid | |
|---|---|
| Ingredient | Parts by Weight of Finished Tablet |
| Fatty material (chocolate or synthetic chocolate) | 35 to 45 |
| Emulsifier | 0.1 to 1 |
| Bulking material (antacid) | 25 to 35 |
| Flavor (e.g., peppermint oil) | 0.3 to 0.8 |
| Direct compaction vehicle | 30 to 40 |

The finished tablets hardness of the tablets so-produced is not directly related to compression pressure. In fact, tablets produced under medium or high pressure (for example, employing pressures of from about 4,000 to about 10,000 psi), in accordance with the method of the present invention, have excellent hardness and flexibility, and lack of brittleness, but are still easily chewed and dissolved in the mouth.

In carrying out the method of the present invention, all ingredients except the direct compaction vehicle will be mixed with the melted fatty material before it is allowed to be recrystallized. Thus, for example, in preparing a compressed chewable confection, or antacid, or other type tablet, the fatty material and emulsifier will be mixed together and heated to melt the fatty material, thereafter, flavor and powdered bulking material are added and mixed until all of the powdered material is absorbed by the melted fatty material. The density and temperature differential of the powdered bulking material should be sufficient to cause the fatty material to recrystallize around the powdered material. As the mixture is continually agitated and allowed to cool, it transforms into a powder. Thereafter, the direct compaction vehicle is added with mixing, the mixture is screened and is then ready for tabletting employing a conventional single punch or other conventional tablet press.

The following Examples represent preferred embodiments of the present invention.

EXAMPLE 1

A soft compressed chewable tablet in the form of a confection having the following composition is prepared as described below.

| Ingredient | Parts by Weight of Tablet |
| --- | --- |
| Ice cap coating (Nestle) (fat, emulsifier, artificial flavor, sugar, milk solids) | 40 |
| Santone 8-1-0 (emulsifier - polyglycerol ester of fatty acids, HLB 13) | 0.5 |
| Chocolate flavor | 0.5 |
| Confectioners sugar | 31 |
| Cantab (dextrose monohydrate) | 28 |

The Ice-cap coating (synthetic chocolate) and emulsifier are melted in a double boiler at 120° F. The melt is transferred to a Hobart type mixer and under agitation the sugar and flavor are added. Mixing is continued for several minutes until all of the powdered material is absorbed by the Ice-cap coating. The density and temperature differential of the powdered material when added to the chocolate causes the chocolate to recrystallize around the material; under continued agitation the mixture, as it cools transforms into a powder which contains in excess of 50% chocolate. Agitation is continued for 5–10 minutes until all of the chocolate or compound coating has recrystallized. The Cantab is then added under agitation. The mixture is screened through a 16 mesh screen and is ready for tabletting. The granulation is then processed through a single punch or other conventional tablet press with a pressure setting of up to 6000 lbs to form the chewable tablets of the invention.

It is found that the so-formed chewable tablet confection of the invention is soft yet flexible and has an excellent chocolate taste.

EXAMPLE 2

A soft compressed chewable antacid tablet having the following composition is prepared as described below.

| Ingredient | Parts by Weight of Tablet |
| --- | --- |
| Ice cap coating | 40 |
| Santone 8-1-0 | 0.5 |
| Peppermint oil | 0.4 |
| CaCO$_3$ | 17.4 |
| Simethicone LVA | 1.3 |
| Al(OH)$_3$ | 6.5 |
| Mg(OH)$_2$ | 5.4 |
| Cantab | 28.5 |

The Ice-cap coating and emulsifier are melted in a double boiler at 120° F. The melt is transferred to a Hobart-type mixer and under agitation the peppermint oil, CaCO$_3$, simethicone, Al(OH)$_3$ and Mg(OH)$_2$ are added. Mixing is continued for an additional 5 minutes until all of the powdered material is absorbed by the Ice-cap coating. The density and temperature differential of the powdered material when added to the melted fatty material will cause the melted fatty material to recrystallize around the powdered material. As the mixture is further mixed and cools, it is transformed into a powder which contains in excess of 50% by weight chocolate (Ice cap coating). After all of the chocolate has recrystallized, the Cantab is added under agitation, the mixture is screened through a 16 mesh screen and is then ready for tabletting.

The granulation is then processed through a single punch tablet press to form the compressed antacid tablets of the invention.

It is found that the so-formed chewable antacid tablet of the invention is soft, yet flexible, has an excellent chocolate, yet non-gritty taste, and is an excellent antacid.

EXAMPLE 3

A chewable vitamin tablet having a final weight of 1 g is prepared as described in Example 2 except that the active ingredient (bulking material) is composed of

| Ingredient | Per 250 mg (100% U.S.R.D.A.) |
| --- | --- |
| Vitamin C | 75 mg |
| Niacinamide | 22 mg |
| Pyridoxine hydrochloride | 2.9 mg |
| Riboflavin | 2 mg |
| Thiamine Mononitrate | 1.8 mg |
| Vitamin A | 6000 I.U. |
| Iron, Electrolytic | 20 mg |

EXAMPLE 4

A chewable aspirin tablet having a final piece weight of 3 g is prepared as described in Example 2 except that the active ingredient (bulking material) is composed of salicylic acid. The chewable tablet will provide approximately 750 mg salicylic acid per dose.

EXAMPLE 5

A chewable analgesic tablet is prepared as described in Example 4 except that the active ingredient is acetaminophen.

What is claimed is:

1. A compressed chewable antacid tablet having good breakage resistance and flexibility which comprises particles of a recrystallized fatty material comprising chocolate, synthetic chocolate or hydrogenated tallow, an antacid bound up in said particles of recrystallized fatty material, and a direct compaction vehicle which binds said particles of recrystallized fatty material and antacid, under compression, into a chewable tablet, said direct compaction vehicle comprising sorbitol, mannitol, dextrose monohydrate, anhydrous lactose, dicalcium phosphate dihydrate, co-crystallized sucrose with modified dextrins, cerelose or other corn syrup solids.

2. The compressed chewable tablet as defined in claim 1 wherein said fatty material is present in an amount up to about 50% by weight of said compressed chewable tablet.

3. The compressed chewable tablet as defined in claim 2 wherein said fatty material is chocolate or synthetic chocolate which contains up to about 40% by weight hydrogenated fat based on the weight of the chewable tablet.

4. The compressed chewable tablet as defined in claim 1 wherein said antacid is present in an amount of from about 10 to about 50% by weight of said chewable tablet.

5. The compressed chewable tablet as defined in claim 1 wherein said direct compression vehicle is present in an amount of at least 25% by weight of said compressed chewable tablet.

6. The compressed chewable tablet as defined in claim 1 wherein said fatty material is present in an amount within the range of from about 35 to about 45% by weight of said compressed chewable tablet.

7. The compressed chewable tablet as defined in claim 1 wherein said antacid is present in an amount within the range of from about 15 to about 35% by weight of said compressed chewable tablet.

8. The compressed chewable tablet as defined in claim 1 wherein said direct compression vehicle is present in an amount within the range of from about 30 to about 40% by weight of said compressed chewable tablet.

9. The compressed chewable tablet as defined in claim 1 wherein said fatty material is chocolate.

10. The compressed chewable tablet as defined in claim 1 wherein said antacid is aluminum hydroxide, calcium carbonate, magnesium carbonate, magnesium hydroxide or mixtures thereof.

11. A method for forming the compressed chewable tablet as defined in claim 1 which comprises melting the fatty material, adding said antacid to said melted fatty material, allowing said melted fatty material containing said antacid to recrystallize and form particles thereof, mixing said particles with direct compaction vehicles and forming a compressed chewable tablet from the resulting mixture.

12. The method as defined in claim 11 wherein said particles of recrystallized fatty material and antacid having an average particle size of within the range of from about 200 to about 1100 microns.

* * * * *